United States Patent
Gozansky

(10) Patent No.: US 6,946,842 B2
(45) Date of Patent: Sep. 20, 2005

(54) ANALYTICAL INSTRUMENT AND PROCESSES

(76) Inventor: Elliott Kirk Gozansky, 2371 Stone Rd., Ann Arbor, MI (US) 48105

(*) Notice: Subject to any disclaimer, the term of this patent is extended or adjusted under 35 U.S.C. 154(b) by 0 days.

(21) Appl. No.: 10/856,446

(22) Filed: May 28, 2004

(65) Prior Publication Data

US 2004/0251905 A1 Dec. 16, 2004

Related U.S. Application Data

(60) Provisional application No. 60/473,792, filed on May 28, 2003.

(51) Int. Cl.[7] .................. G01V 3/00; A61B 5/055
(52) U.S. Cl. ........................ 324/318; 600/410
(58) Field of Search ........................ 73/23.2, 23.36, 73/23.41; 324/300–322; 128/845, 846; 607/96; 436/518, 37; 601/16; 49/507; 604/262; 454/187; 414/217.1; 134/6; 600/410

(56) References Cited

U.S. PATENT DOCUMENTS

| | | | |
|---|---|---|---|
| 2,702,034 A | * 2/1955 | Walter | 604/262 |
| 4,676,144 A | * 6/1987 | Smith, III | 454/187 |
| 4,817,644 A | * 4/1989 | Holmes et al. | 134/6 |
| 5,192,910 A | 3/1993 | Hepp et al. | 324/315 |
| 5,451,131 A | * 9/1995 | Hecht et al. | 414/217.1 |
| 6,410,331 B1 | 6/2002 | Schultz et al. | 436/37 |
| 6,418,932 B2 | 7/2002 | Paschal et al. | 128/845 |
| 6,553,722 B1 | * 4/2003 | Porret et al. | 49/507 |
| 6,817,143 B2 | * 11/2004 | Porret et al. | 49/507 |
| 2001/0029955 A1 | 10/2001 | Paschal et al. | 128/846 |
| 2002/0133100 A1 | 9/2002 | Paschal et al. | 601/16 |
| 2003/0015019 A1 | 1/2003 | O'Brien | 73/23.2 |
| 2003/0027359 A1 | 2/2003 | Hudak et al. | 436/518 |
| 2003/0126799 A1 | * 7/2003 | Porret et al. | 49/507 |
| 2004/0035183 A1 | 2/2004 | O'Brien et al. | 73/23.36 |
| 2004/0215294 A1 | 10/2004 | Littrup et al. | 607/96 |
| 2004/0251905 A1 | * 12/2004 | Gozansky | 324/321 |

* cited by examiner

*Primary Examiner*—Brij Shrivastav
*Assistant Examiner*—Tiffany A. Fetzner
(74) *Attorney, Agent, or Firm*—Mayer, Brown, Rowe & Maw LLP

(57) ABSTRACT

An analytical instrument for analyzing biohazardous specimens is provided. The instrument provides means for exposing only the sample chamber to the containment area. A process for analyzing a biohazardous sample is also provided.

9 Claims, 2 Drawing Sheets

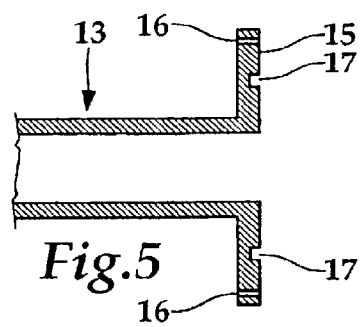
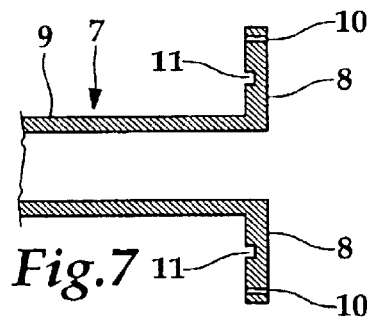
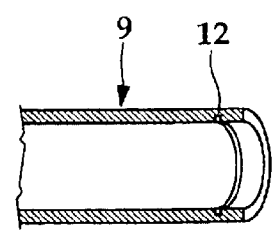
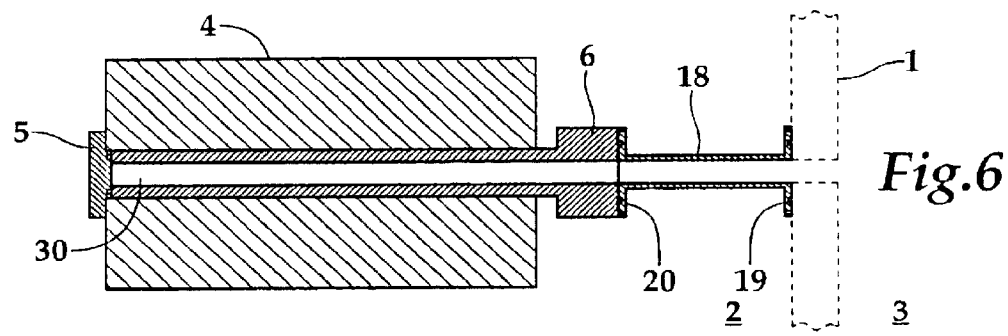
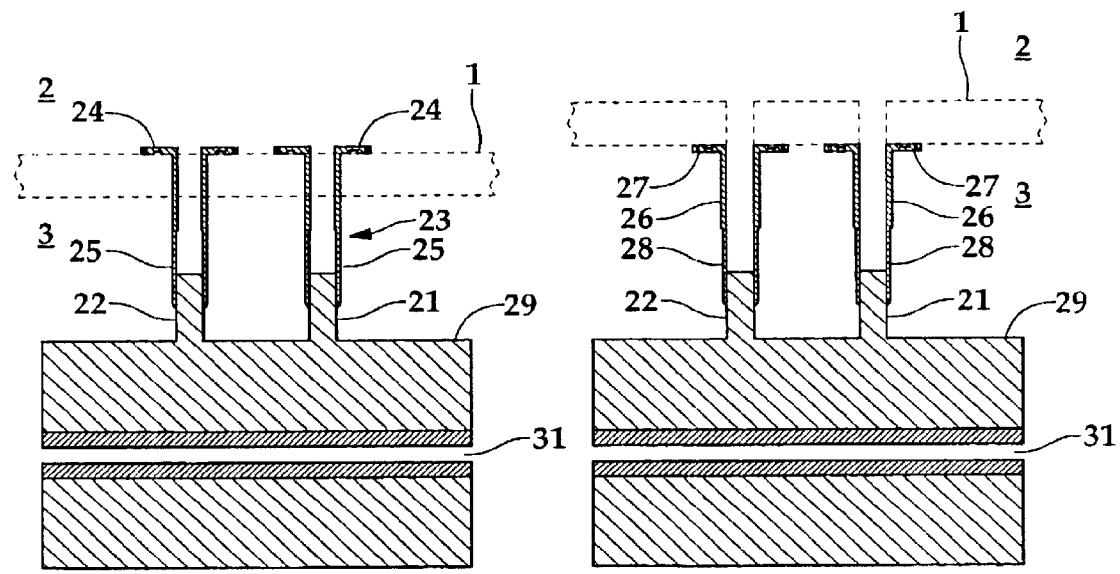

ANALYTICAL INSTRUMENT AND PROCESSES

CROSS REFERENCE TO RELATED APPLICATIONS

This application claims priority to application Ser. No. 60/473,792, filed on May 28, 2003.

FEDERALLY SPONSORED RESEARCH

Not applicable.

REFERENCE TO MICROFICHE APPENDIX

Not applicable.

FIELD OF THE INVENTION

This invention relates to an interface between a biohazard containment area and a laboratory or clinical analytical instrument. The invention further relates to processes for analyzing biohazardous specimens and samples using an instrument of which only the sample chamber is exposed to the biohazardous environment.

BACKGROUND OF THE INVENTION

Researchers conduct research on microbiological pathogens which, if allowed to escape into the environment, could cause severe illness and/or fatalities among human and/or animal populations. Similarly, clinicians conduct studies on human and animal subjects infected with such pathogens or with experimental vaccines against or treatments for such pathogens. The compositions utilized in the clinical studies are also frequently pathogenic or potentially pathogenic, such as in the case of live virus vaccines. In yet other studies, experimental subjects, both plant and animal, may be subjected to retroviral treatment to produce transgenics which may produce unique pathogenic microbes. Thus, it is important that a large part of such activities be conducted in secure environments from which accidental release of the pathogens is prevented. The Centers for Disease Control and Prevention has established a Biosafety Level rating systems which is used to determine the type of facility and procedures to be used in handling infectious agents.

The highest Biosafety Level, BSL 4, is reserved for the most dangerous infectious agents. BSL 4 rated agents are handled in containment facilities having specialized ventilation and plumbing systems. Moreover, BSL 4 facilities have specialized entry and exit procedures. Biosafety Level 4 facilities are quite expensive due to the specialized systems and requirements. Moreover, there are few such facilities in the country available to researchers and clinicians. Thus, the value of BSL 4 facility per square foot is quite high and efforts are made to minimize bulky equipment placed in such facility so as to maximize working and habitat space. Furthermore, equipment in a BSL 3 or 4 environment must be autoclaved or otherwise sterilized before being removed from the containment area. To autoclave large pieces of analytical or diagnostic equipment, however, would be prohibitive.

SUMMARY OF THE INVENTION

Embodiments of the invention provide an analytical instrument including: a sample chamber located in a clean environment; means for connecting the sample chamber with a containment area wherein the means permit placement of an analytical sample into the sample chamber and wherein the means are hermetically sealed against contamination of the clean environment; and means for hermetically sealing the sample chamber from the clean environment.

The analytical instrument may be for example, an MRI, NMR, mass spectroscope, infrared spectroscope, ultraviolet spectroscope, or visible spectroscope.

In some embodiments of the invention, the connection includes an opening in a barrier between the clean environment and the containment area; a flange comprising a piping portion and an annular portion wherein the piping portion passes through the opening and extends into the clean environment, wherein the annular portion is attached to the containment area side of the barrier; and wherein the piping portion which extends into the clean environment is in hermetic communication with the sample chamber.

In some embodiments of the invention, an analytical instrument including a sample chamber located in a containment area; means for connecting the sample chamber with associated components located in a clean environment wherein the means are hermetically sealed against contamination of the clean environment, is provided.

BRIEF DESCRIPTION OF THE DRAWINGS

FIG. 5 is a cross-section view of an embodiment of a flange useful in the invention.

FIG. 6 is a cross-section view of a fourth embodiment of the analytical instrument of the invention.

FIG. 7 is a cross-section view of a second embodiment of a flange useful in the invention.

FIG. 8 is a cross-section view of a portion of a flange useful in the invention.

FIG. 9 is a cross-section view of a fifth embodiment of the analytical instrument of the invention.

FIG. 10 is a cross-section view of a sixth embodiment of the analytical instrument of the invention.

DESCRIPTION OF EMBODIMENTS OF THE INVENTION

As used herein the term "containment area" refers to an enclosure for housing infectious and/or biohazardous biological samples, humans and/or animals. Containment areas include, for example, enclosures having Biosafety Levels ("BSL") 3 and 4 as defined by the Centers for Disease Control. Containment areas may include, for example, isolated buildings, rooms, or cabinets. In preferred embodiments of the invention, the containment area has a BSL 4 rating.

As used herein, the term "clean environment" means any area located near or adjacent to a containment area and which is substantially free of infectious and/or biohazardous biological samples, humans and/or animals.

As used herein, the term "analytical instrument" means any type of equipment, including, for example, mass, nuclear magnetic resonance, infrared, visible and ultraviolet spectroscopes, and chromatographs used to detect and/or measure characteristics or properties of any type of sample.

As used herein, the term "associated components" means those parts of an analytical instrument other than the sample or specimen chamber and components which, of necessity, are about or surround the sample or specimen chamber.

Figure 1:
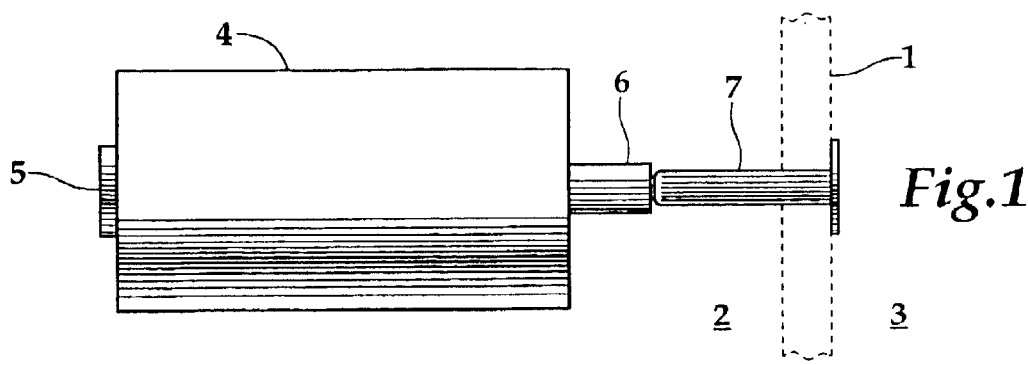
FIG. 1 is a side view of a first embodiment of the analytical instrument of the invention.
Figure 2:
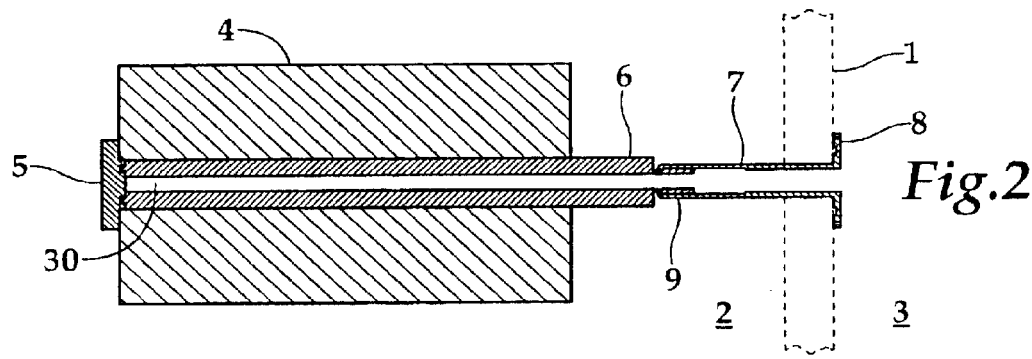
FIG. 2 is a cross-section view of the embodiment depicted in FIG. 1.

Referring now to FIG. 1, a side view of a first embodiment of an analytical instrument of the invention is shown. The structure 1 shown by a dotted line represents a barrier between a clean environment 2 and a containment area 3. FIG. 2 shows a cross-section of the instrument shown in FIG. 1. A sample chamber 30 is contained within a housing 4. A flange or cap 5 forms a hermetic seal between clean environment 2, and sample chamber 30, which is in communication with containment area 3. Sample chamber 30 includes a cuff 6 extending outside of housing 4. Hermetically connected to cuff 6 is a piping portion 9 of a flange 7. The piping portion of flange 7 extends through an opening in barrier 1 and terminates in an annular portion 8 in the containment area 3. Annular portion 8 may be attached to the containment area side of barrier 1 by any of a number of known means, including bolts, epoxy or other sealants. All or part of the interfacial area between flange 7 and barrier 1 is hermetically sealed.

Referring now to FIG. 7, a cross-sectional view of flange 7 is shown. Annular portion 8 may include one or more openings 10 through which bolts may attach to barrier 1. Annular portion 8 may further include one or more groves 11 into which o-rings may be seated. In other embodiments of flange 7, no grooves 11 are present. An epoxy or other acceptable sealant may be used to seal the interface between annular portion 8 and the containment area side of barrier 1.

Referring now to FIG. 8, the piping portion 9 of flange 7 is shown in cross-section. In some embodiments one or more grooves 12 are located on the internal surface of piping portion 9 into which o-rings may be seated to form a hermetic seal with cuff 6. In alternative embodiments, cuff 6 may contain one or more grooves and o-rings for placement over piping portion 9. In yet other embodiments, cuff 6 and piping portion 9 may be hermetically sealed by epoxy or other sealant or by means of welding or other permanent affixation.

Figure 3:
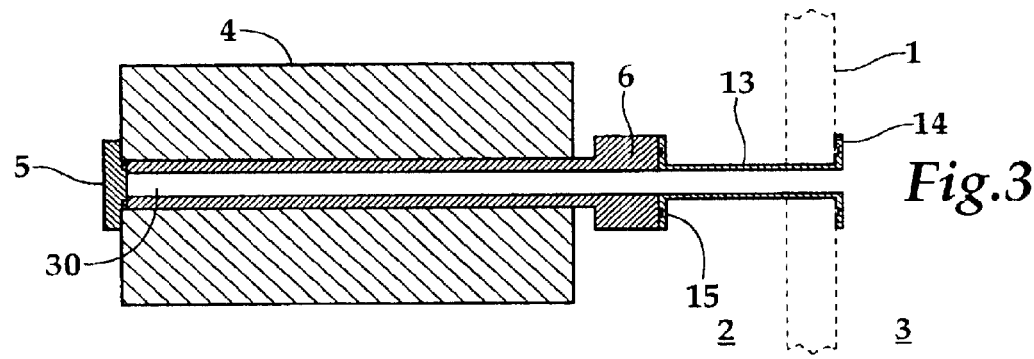
FIG. 3 is a cross-section view of a second embodiment of the analytical instrument of the invention.

FIG. 3 shows an alternative embodiment of the analytical instrument in which a flange 13 includes two annular portions 14 and 15.

Annular portion 14 may be attached to the containment area side of barrier 1 as discussed in connection with FIGS. 2 and 7. Annular portion 15 may be attached to cuff 6 using any of a known number of means including temporary means, such as bolts, epoxy or other sealant, or permanent affixation means such as welding.

Referring now to FIG. 5, annular portion 15 is shown in more detail. Annular portion 15 may in some embodiments, include one or more grooves 17 into which o-rings may be seated.

FIG. 6 depicts another embodiment of the invention in which no portion of flange 18 passes through barrier 1. Flange 18 includes two annular portions 19 and 20, each of the type shown in FIG. 5. Annular portion 19 is attached to the clean environment side of barrier 1 such that it completely and hermetically seals around the opening in barrier 1.

Figure 4:
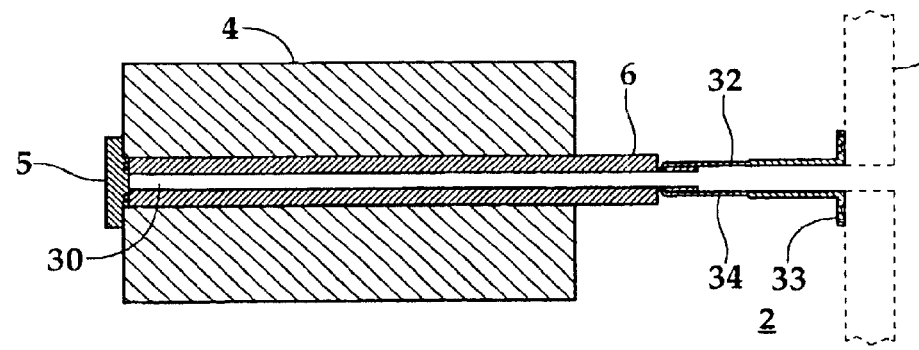
FIG. 4 is a cross-section view of a third embodiment of the analytical instrument of the invention.

In yet another embodiment of the invention, shown in FIG. 4, a flange 32 having an annular portion 33 of the type shown in FIG. 5 is attached to the clean environment side of barrier 1. Flange 32 further includes a piping portion 34 of the type shown in FIG. 8 for connection to cuff 6.

Other embodiments of means for communication between sample chamber 30 and the containment area 3 may be envisioned and are contemplated within the scope of the invention. For example, one end of flange 18, 13, or 7 may be embedded within barrier 1. In yet other embodiments, cuff 6 is optional and may be absent depending upon the type of analytical instrument. In those embodiments without a cuff, the flange attached directly to a sample chamber opening.

FIG. 9 shows an alternative configuration of the invention in which a portion of the analytical instrument is located within the containment area 3. As shown in FIG. 9, the analytical instrument is an MRI and the specimen chamber 31 is surrounded by a housing 29 which contains a cryogenic circulation loop. The cryogenic circulation loop receives coolant through a port 21 and the coolant exits the loop through a port 22. Ports 21 and 22 communicate with a coolant cooling and circulation system, including for example pumps and condensate traps which are located in clean environment 2. In such embodiments, each of ports 20 and 21 are each hermetically attached to a flange 23. Flanges 23 may include an annular portion 24 and a piping portion 25. As shown in FIG. 9, annular portion 24 is of the type shown and described in FIG. 7 and piping section 25 is as shown and described in FIG. 8. In alternative embodiments, flanges of the types are shown in FIG. 3. In alternative embodiments, there may be only one port for receiving a cryogenic fluid and an exhaust port for release of gaseous, used coolant. In yet other embodiments, the sample chamber is surrounded by a jacket, not cooling coils, into which coolant is pumped.

As shown in FIG. 9 a portion of flange 23 passes through barrier 1. FIG. 10 shows another embodiment in which the flange connecting ports 21 and 22 to the remainder of the cryogenic cooling system, i.e. associated components, attached to the containment area side of barrier 1.

In yet other embodiments of the invention the analytical instrument may have other associated components, such as computer interfaces, motors, pumps, analyte or diluents reservoirs, etc . . . Such associated components may be located in a clean environment and connected to the sample chamber through appropriate flange schemes.

What is claimed is:

1. An imaging or spectroscopic analytical instrument comprising:

a sample chamber surrounded by a clean environment and in communication with a containment area capable of enclosing Biosafety Level 3 and/or 4 material as defined by the Center for Disease Control;

means for connecting the sample chamber with a containment area for exposing only the sample chamber to the containment area wherein the connection means permits placement of an analytical sample into the sample chamber and wherein the connection means is hermetically sealed against contamination of the clean environment; and means for hermetically sealing the sample chamber from the clean environment.

2. The imaging or spectroscopic analytical instrument of claim 1, wherein the imaging or spectroscopic analytical instrument is an MRI.

3. The imaging or spectroscopic analytical instrument of claim 1 wherein the imaging or spectroscopic analytical instrument is selected from the group of: nuclear magnetic resonance spectroscope, mass spectroscope, infrared spectroscope, ultraviolet spectroscope, and visible spectroscope.

4. The imaging or spectroscopic analytical instrument of claim 1 wherein the connection means comprises:
   an opening in a barrier between the clean environment and the containment area;
   a flange comprising a piping portion and an annular portion wherein the piping portion passes through the opening and extends into the clean environment, wherein the annular portion is attached to the containment area side of the barrier; and wherein the piping portion, which extends into the clean environment is in hermetic communication with the sample chamber.

5. The imaging or spectroscopic analytical instrument of claim 4 wherein the attachment of the annular portion to the containment area side of the barrier forms a hermetic seal.

6. The imaging or spectroscopic analytical instrument of claim 4 wherein the piping portion passing through the opening is hermetically sealed to the opening.

7. The imaging or spectroscopic analytical instrument of claim 1 wherein the connection means comprises;
   an opening in a barrier between the clean environment and the containment area;
   a flange comprising an annular portion wherein the annular portion is attached to the clean environment side of the barrier such that the annular portion surrounds the opening.

8. An imaging or spectroscopic analytical instrument comprising:
   a sample chamber located in a containment area capable of enclosing Biosafety Level 3 and/or 4 material as defined by the Center for Disease Control;
   means for connecting the sample chamber with associated components of the imaging or spectroscopic analytical instrument located in a clean environment wherein the connection means is hermetically sealed against contamination of the clean environment.

9. The imaging or spectroscopic analytical instrument of claim 8 wherein the imaging or spectroscopic analytical instrument is an MRI, and further comprising a cryogenic coolant jacket surrounding the sample chamber, and wherein the associated components of the imaging or spectroscopic analytical instrument comprise a cryogenic cooling system.

* * * * *